United States Patent
Wilhelm et al.

(10) Patent No.: US 10,676,445 B1
(45) Date of Patent: Jun. 9, 2020

(54) SYNTHESIS OF AMINOPYRIMIDINE-BASED ENERGETIC MATERIALS

(71) Applicant: The United States of America as Represented by the Secretary of the Navy, Indian Head, MD (US)

(72) Inventors: Christopher Wilhelm, Port Tobacco, MD (US); Farhad Forohar, LaPlata, MD (US); Denisse Soto, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/501,761

(22) Filed: Jun. 6, 2019

(51) Int. Cl.
  *C07D 239/48* (2006.01)
  *C07D 239/50* (2006.01)

(52) U.S. Cl.
  CPC .......... *C07D 239/48* (2013.01); *C07D 239/50* (2013.01)

(58) Field of Classification Search
  CPC .................................................. C07D 239/50
  USPC ........................................................ 544/323
  See application file for complete search history.

(56) References Cited

U.S. PATENT DOCUMENTS

| | | | |
|---|---|---|---|
| 3,455,921 A * | 7/1969 | Wagner | C07D 239/30 544/323 |
| 5,705,309 A | 1/1998 | West et al. | |

OTHER PUBLICATIONS

PubChem CID 129985563 (create date: 2017).*
PubChem SID 343132076 (deposit date: 2017).*
Liu et al., 2,4-diazido-5-iodo-pyrimidine crystal under high pressure: A comparison of DFT and DFT-D studies, Computational and Theoretical Chemistry, 1000, pp. 60-69 (2012).*
Temple, Jr. et al., Studies on the Azidoazomethine-tetrazole equilibrium. II. 4-Azidopyrimidines, Journal of Organic Chemistry, vol. 30, pp. 829-834 (Mar. 1965).*
Temple, Jr. et al., Studies on the Azidoazomethine-tetrazole equilibrium. I. 2-Azidopyrimidines, Journal of Organic Chemistry, vol. 30, pp. 826-829 (Mar. 1965).*
Polyazido Pyrimidines: High Energy Compounds, Dr. C. Ye et al. http://citeseerx.ist.psu.edu/viewdoc/download?doi=10.1.1.1009.3288 &rep=rep1&type=pdf, (2006).
https://www.researchgate.net/publication/264514646_4-Amino-26-di-chloro-5-nitro-pyrimidine, (2004).
Synthesis, structure and properties of 2,4,6-triazido-pyrimidine-5-carbonitrile https://www.arkat.usa.org/get-file/63627/, (2018).

* cited by examiner

*Primary Examiner* — Deepak R Rao
(74) *Attorney, Agent, or Firm* — Frederic J. Zimmerman (57) ABSTRACT

A new azido compound, 5-amino-6-chloro-2,4-diazido-pyrimidine, and a process for synthesizing. The synthesis may include reacting 5-amino-2,4,6-trichloropyrimidine and sodium azide. There is an excess molar amount of sodium azide for each chloro fractional molar amount on the 5-amino-2,4,6-trichloropyrimidine. The synthesis is a two phase reaction that is a dispersion. The 5-amino-2,4,6-trichloropyrimidine dissolved in acetone is a liquid phase, and the sodium azide is insoluble in acetone and is a solid phase, that is present in excess of chemical equivalents. The reaction product is soluble in acetone, and the reaction by-product, sodium chloride is also insoluble in acetone, and the crude yield is about 92%. Unreacted sodium azide and formed sodium chloride are removed by filtration.

8 Claims, 7 Drawing Sheets

X-ray Crystallography of 5-amino-6-chloro-2,4-diazido-pyrimidine

SYNTHESIS OF AMINOPYRIMIDINE-BASED ENERGETIC MATERIALS

STATEMENT OF GOVERNMENT INTEREST

The invention described herein may be manufactured and used by or for the Government of the United States of America for Governmental purposes without the payment of any royalties thereon or therefore.

FIELD OF THE INVENTION

The invention relates generally to the synthesis of azide compounds that could be converted to nitro compounds, and more particularly to a new azido amino-pyrimidine compound, 5-amino-6-chloro-2,4-diazido-pyrimidine, that can be converted to a nitro compound with at least one vicinal amine group, wherein the nitro compound would be a relatively insensitive munition.

BACKGROUND OF THE INVENTION

Conventional technology teaches a photosensitive composition that contains polyazide. The composition is an infrared absorber in a photo-crosslinkable binder. Examples of other useful polyazides include 2,4,6-triazido-s-triazine, 2,4-diazido-s-triazine, 2,4-diazido-6-methyl-s-triazine, 2,4,6-triazidopyrimidine, 2,4-diazido-6-methylpyrimidine, 2,4-diazido-6-phenylaminopyrimidine.

TATB, triaminotrinitrobenzene or 2,4,6-triamino-1,3,5-trinitrobenzene is an explosive that has a benzene ring structure with three nitro functional groups ($NO_2$) and three amine ($NH_2$) groups attached, alternating around the ring.

TATB is a powerful explosive that is slightly less powerful than RDX (i.e. 1,3,5-Trinitro-1,3,5-triazacyclohexane), but more than TNT). TATB is extremely insensitive to shock, vibration, fire, or impact. Since TATB is so difficult to detonate by accident, even under severe conditions, it has become preferred for applications where extreme safety is required. For example, the explosives used in nuclear weapons, where accidental detonation during an airplane crash or rocket misfiring would present extreme dangers.

TATB is normally used as the explosive ingredient in plastic bonded explosive compositions, such as a polymer-bonded explosive, also called PBX or plastic-bonded explosive. The explosive material is bound together in a matrix using a synthetic polymer.

Not all organic nitro compounds are used exclusively for explosives. A variation of the explosive used in dynamite, nitroglycerin, is also a medication used for heart failure, high blood pressure, and to prevent chest pain symptomatic of not enough blood flow to the heart (angina). Chest pain in men precedes or is accompanies a heart attack. It is taken by mouth, under the tongue, applied to the skin, or by injection into a vein. Compounds with even slight solubility in water often have applications in pharmaceutical chemistry and other biocompatible reactions.

SUMMARY OF THE INVENTION

The invention is a new azido amino-pyrimidine compound, 5-amino-6-chloro-2,4-diazido-pyrimidine, which is also known as 6-chloro-2,4-diazido-pyrimidin-5-amine. 5-amino-6-chloro-2,4-diazido-pyrimidine is the major reaction product of 5-amino-2,4,6-trichloro-pyrimidine and an aziding reagent, such as sodium azide. The reaction product, 5-amino-6-chloro-2,4-diazido-pyrimidine, may be safely prepared and purified in high yields.

An object of the invention is to prepare a compound that may be converted into one with nitro groups, wherein at least one nitro group will have a vicinal amine group, and the hydrogen bonding between the amine group and the nitro groups help make an energetic material less sensitive. Azido compounds are known to be suitable precursors that may be facilely converted to nitro compounds. The invented diazido precursor, 5-amino-6-chloro-2,4-diazido-pyrimidine, is a precursor to a dinitro compound, 5-amino-6-chloro-2,4-dinitro-pyrimidine. Both 5-amino-6-chloro-2,4-diazido-pyrimidine and 5-amino-6-chloro-2,4-dinitro-pyrimidine are new compounds.

A second object of the invention is that the 5-amino-6-chloro-2,4-diazido-pyrimidine may be readily isolated from potentially reactive agents, and in particular aziding agents.

A third object of the invention is that the synthesis of should be relatively straight forward, in that purification is easily accomplished and yields are at least 50%.

A fourth object of the invention is that the 5-amino-6-chloro-2,4-diazido-pyrimidine may be potentially used in further reactions, for example to be polymerized, coupled, or modified.

A final object of the invention is that azido compounds are very useful precursors to a variety of nitrogen rich compounds, and nitrogen rich compounds are used in "click" chemistry to make triazole containing products. The reader is reminded that in a click chemical synthesis, biocompatible reactions are primarily used to join substrates with specific biomolecules. Click chemistry describes a way of generating products that are found in nature, and the products are often insensitive to oxygen and water. In some cases water is an ideal reaction solvent, providing the best yields and highest rates. If the 6-chloro-2,4-diazido-pyrimidine has applications in click chemistry, then this structure would be an additional pharmaceutical chemical tool.

BRIEF DESCRIPTION OF THE DRAWINGS

The foregoing invention will become readily apparent by referring to the following detailed description and the appended drawings in which.

DETAILED DESCRIPTION OF THE INVENTION

The invention is a new azido compound 5-amino-6-chloro-2,4-diazido-pyrimidine, which is also known as 6-chloro-2,4-diazido-pyrimidin-5-amine.

Figure 1:
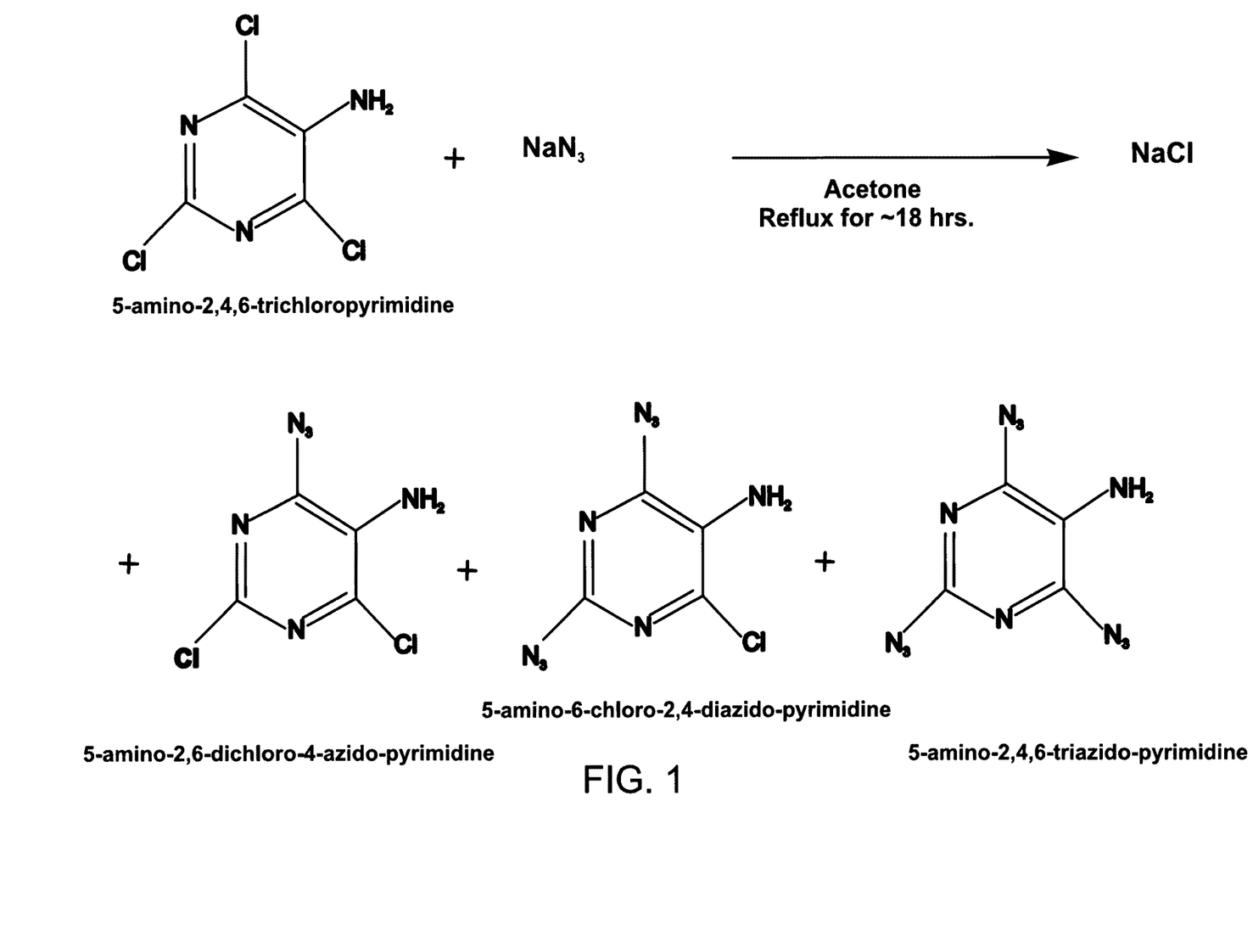
FIG. 1 illustrates the reaction sequence for the synthesis of an amino-azido-pyrimidine, and in particular 5-amino-6-chloro-2,4-diazido-pyrimidine.
Figure 5:
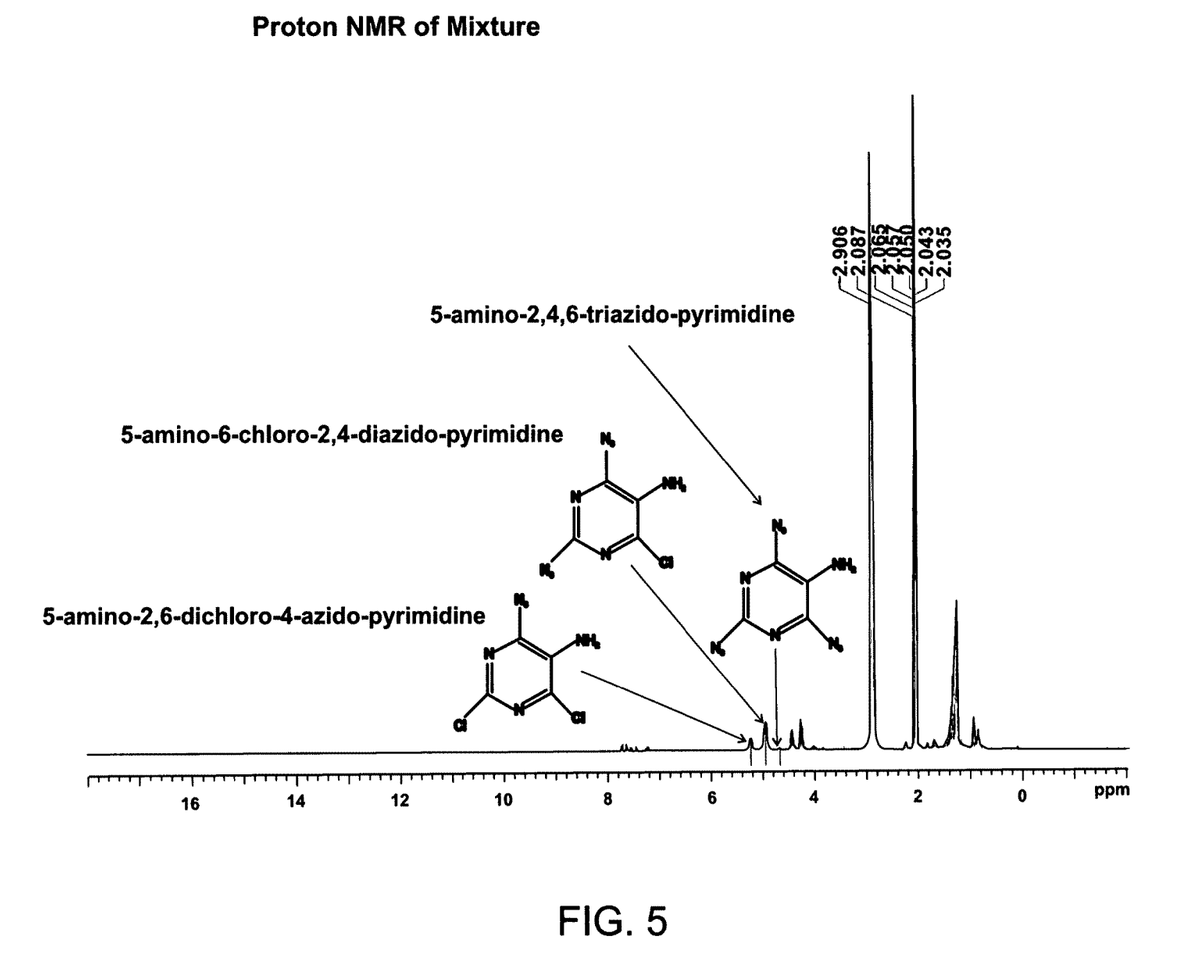
FIG. 5 is the proton NMR spectra of the product mixture.
Figure 6:
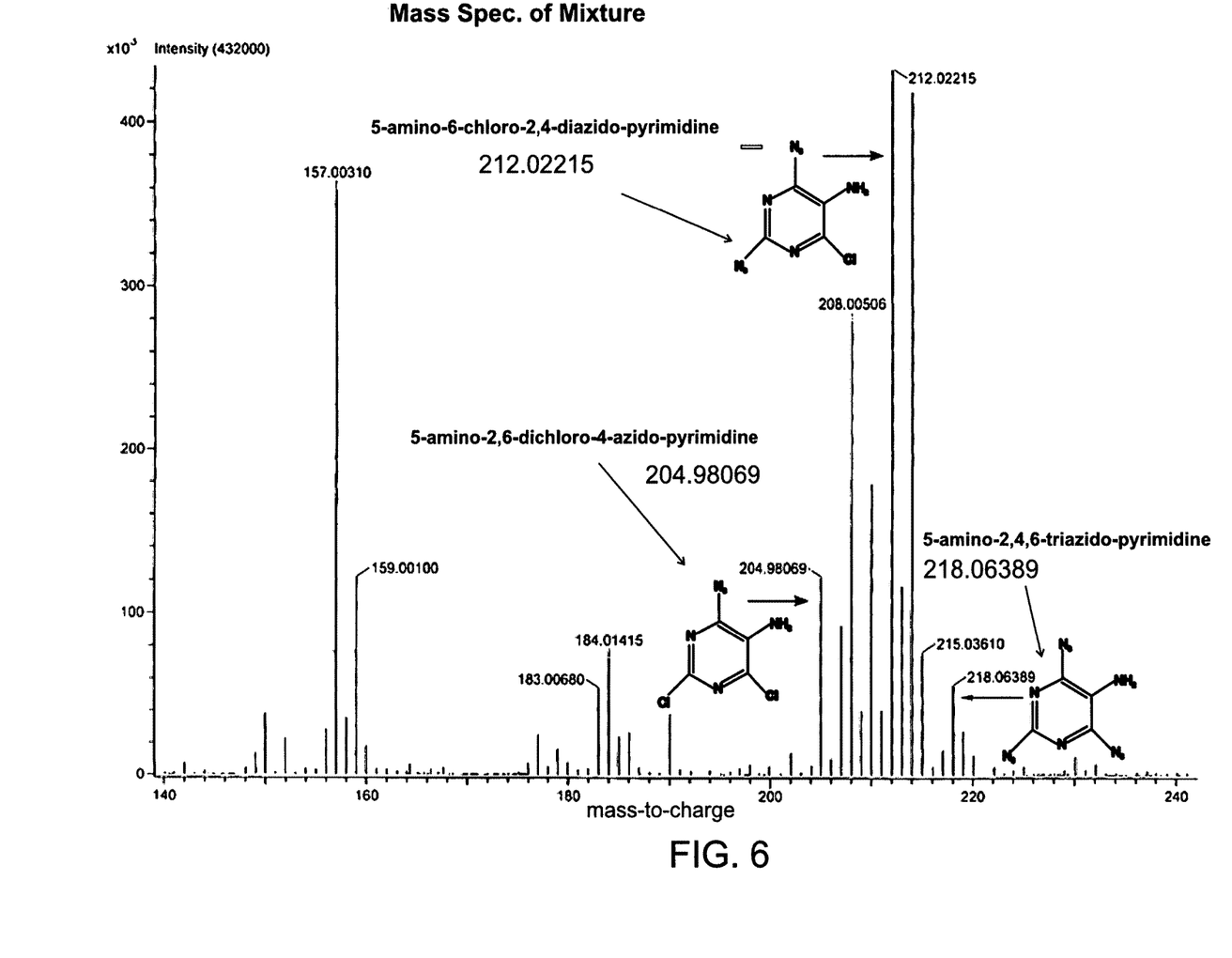
FIG. 6 the mass spectra of the product mixture.

The azido compound, 5-amino-6-chloro-2,4-diazido-pyrimidine, is prepared by reacting an aziding agent, such as sodium azide, with 5-amino-2,4,6-trichloropyrimidine in a solvent (acetone), therein substituting the number 2 and the number 4 chloro atoms with azido groups. The reaction shown in FIG. 1, converts about 94% of the 5-amino-2,4,6-trichloropyrimidine into 5-aminoazido-pyrimidines. As shown in FIG. 5, which is the proton spectra of the product mixture following reflux, and FIG. 6, which is the mass spectrum of the product mixture, there are lesser amounts of 5-amino-2,6-dichloro-4-azido-pyrimidine and very little 5-amino-2,4,6-triazido-pyrimidine. In FIG. 5 the area under the peaks at about 5.22 ppm for 5-amino-2,6-dichloro-4-azido-pyrimidine, about 4.95 ppm for 5-amino-6-chloro-2,4-diazido-pyrimidine, and about 4.68 ppm for 5-amino-2,4,6-triazido-pyrimidine provides a strong indication of the relative amounts of the three formed azido products.

The starting material, 5-amino-2,4,6-trichloro-pyrimidine, is known, and is generally sold under the IUPAC name as 2,4,6-trichloropyrimidin-5-amine (CAS #91322-00-8), and is available from several companies including Shanghai Run-Biotech Co., Ltd.

Actual Performed Procedure. The experimental procedure for synthesizing 5-amino-6-chloro-2,4-diazido-pyrimidine is as follows:

A suspension of 5-amino-2,4,6-trichloropyrimidine (1.0 g, 5.0 mmol), sodium azide (2.5 g, 38.0 mmol) and 30 ml acetone was refluxed for about 18 hours. The ratio of equivalents was about 1 meq. of each chlorine atom of 5-amino-2,4,6-trichloropyrimidine for every 2.5 meq. of sodium azide (where meq. is milliequivalent). The suspension was then filtered and the filtrate was concentrated at 56° C. to obtain 1.2 g of a yellow-green oil. The oil was extracted with methylene chloride (50 ml) and water (3 times with 30 mls). The organic solution was dried over sodium sulfate ($Na_2SO_4$), filtered, and concentrated. The dried filtered oil weighed about 1.0 g (which is 4.7 mmol or about 94% crude yield).

The oil was allowed to cool to room temperature. After a few minutes at room temperature, the oil turned into a yellow solid. The solid was dispersed in about 7 ml of absolute ethanol, and gently heated until all of the yellow solid has dissolved.

The mixture was allowed to rest over-night at ambient condition. During that time period light yellow crystals formed. The light yellow crystals were collected by filtration and were washed quickly with 3 ml of ice-cold absolute ethanol. The weight of the dried light yellow crystals was about 0.55 g (~2.6 mmol., which is ~52% yield) of 5-amino-6-chloro-2,4-diazidopyrimidine. The melting point was determined to be 94-95° C.

Figure 2:
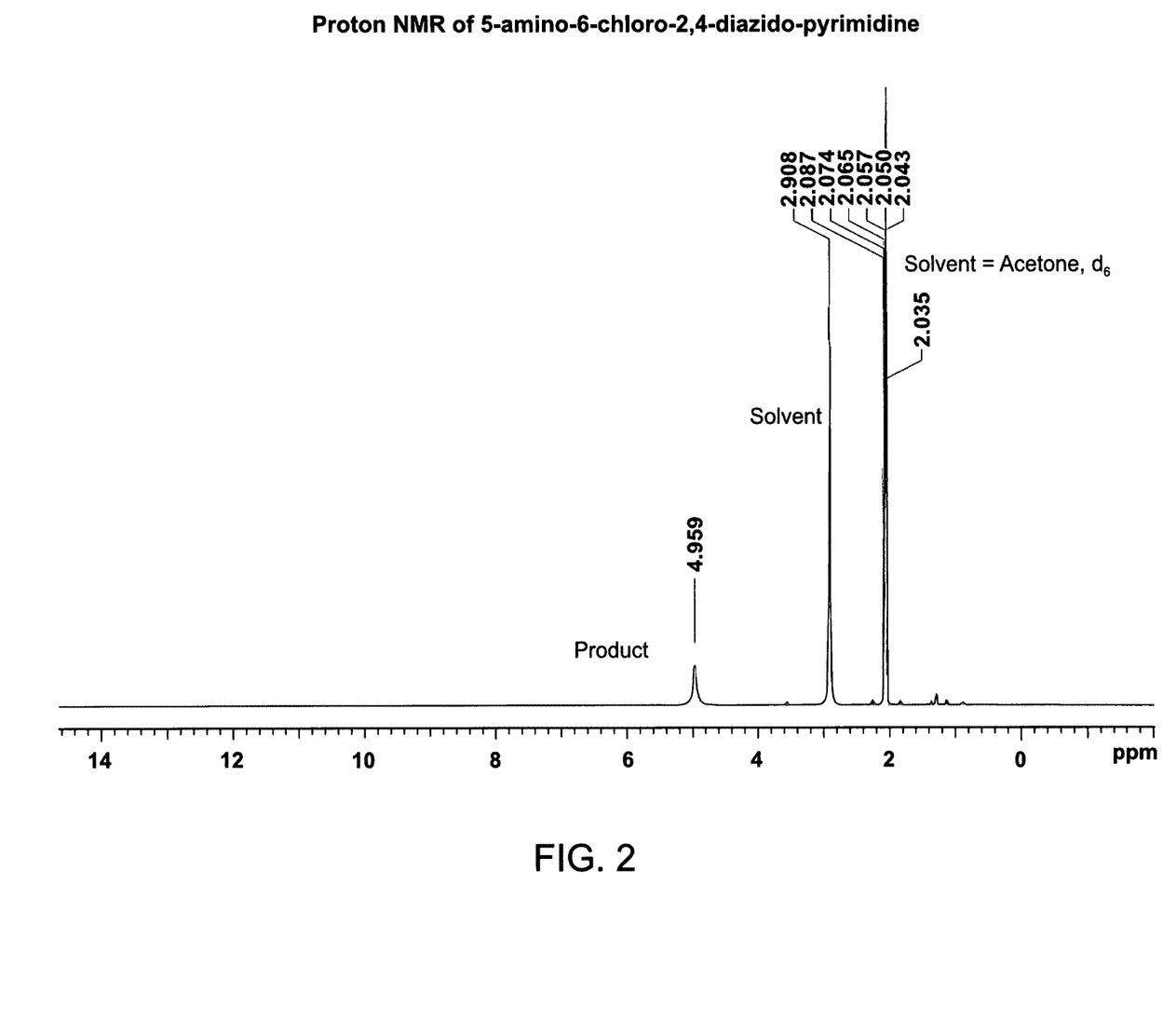
FIG. 2 is the proton NMR spectra of 5-amino-6-chloro-2,4-diazido-pyrimidine, in deuterated acetone (acetone, $d_6$)

The proton NMR spectra in deuterated acetone (300 MHz, $COC_2H_6$) are shown in FIG. 2 and FIG. 5. The amine hydrogens in deuterated acetone have a shift to 4.95 ppm. In deuterated chloroform (300 MHz, $CDCl_3$) the amine hydrogens have a shift to about 3.95 ppm(broad, H).

Figure 3:
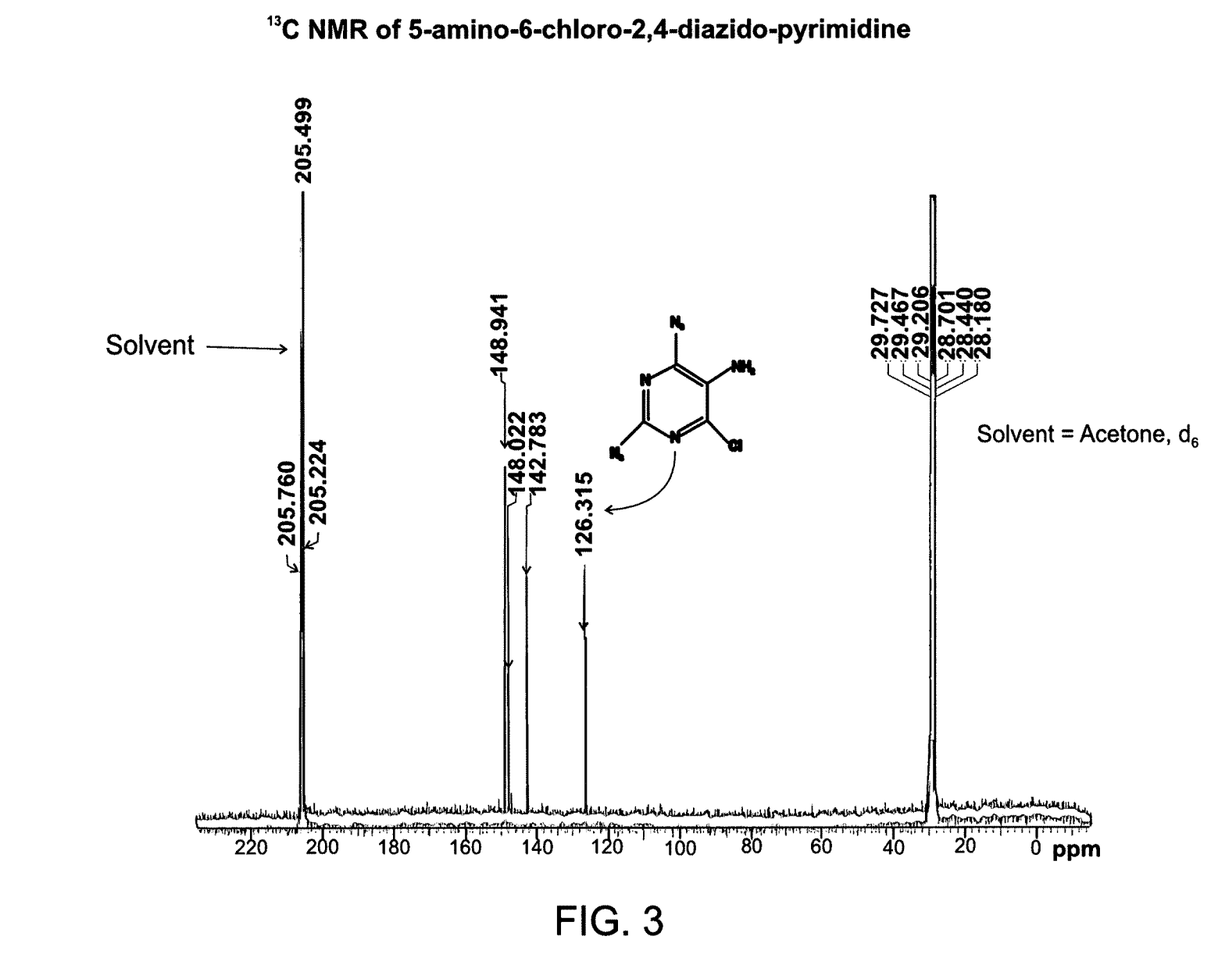
FIG. 3 is the carbon thirteen spectra of 5-amino-6-chloro-2,4-diazido-pyrimidine in acetone $d_6$.
Figure 4:
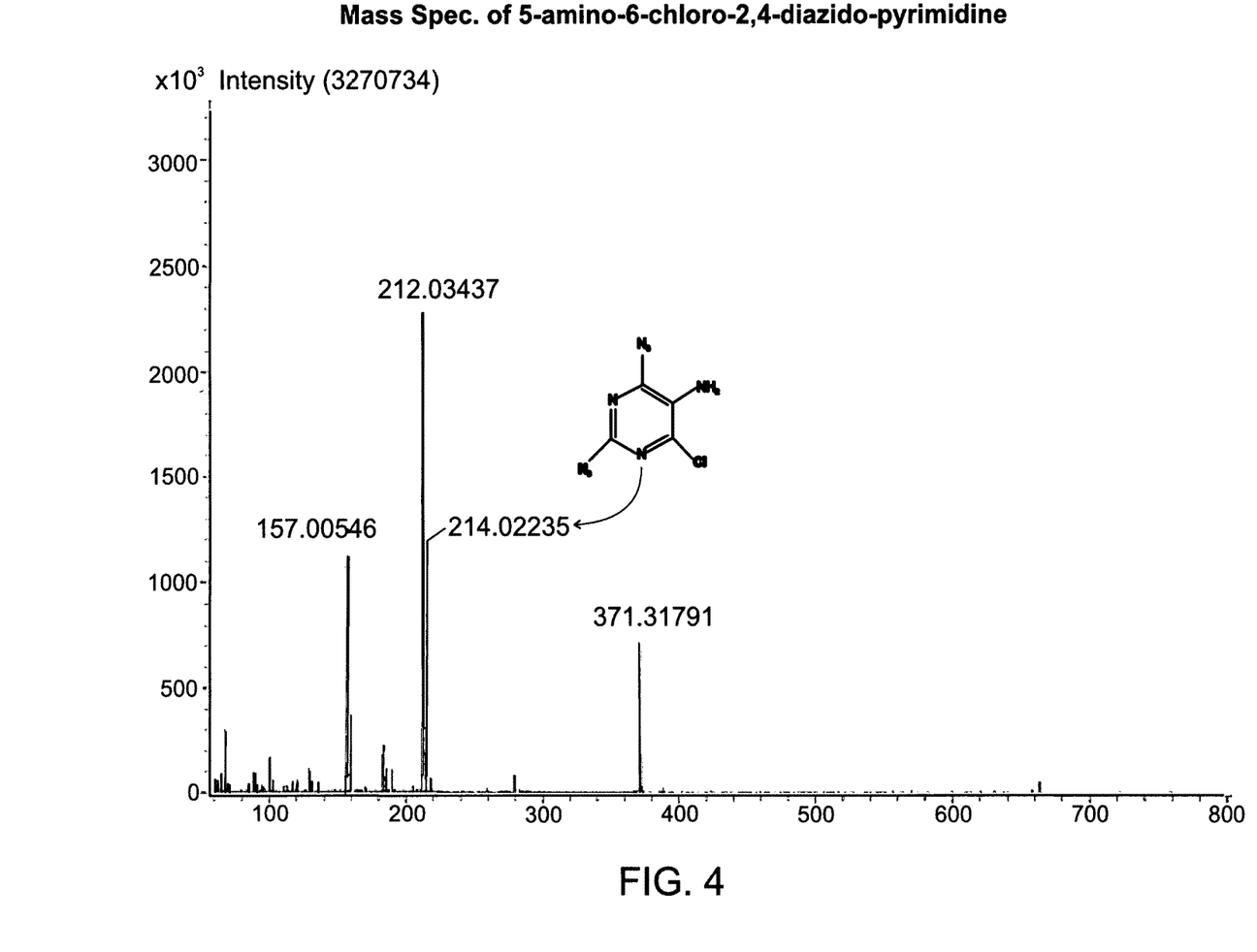
FIG. 4 the mass spectra of 5-amino-6-chloro-2,4-diazido-pyrimidine.

The $^{13}C$ NMR in deuterated acetone $COC_2H_6$, is shown in FIG. 3; 148.941 ppm, 148.022 ppm, 142.783 ppm, and 126.315 ppm. In deuterated chloroform, the chemical shifts are as follows: (300 MHz, $CDCl_3$) δ 149.67 ppm, δ 149.43 ppm, δ 144.16 ppm, δ 124.74 ppm.

The dominate peaks of the Infrared spectra are as follows: 3467 (vw), 3350 (w), 2134 (vs), 1615 (w), 15401 (s), 1418 (m), 1377 (s), 1349 (m), 1232 (m), 1199 (vw), 1146 (w), 991 (vw) $Cm^{-1}$;

The MS-DART ionization-positive (m/z) is as follows: calculated for $C_4H_2ClN_9$ [M+H]+, 212.0122; found, 212.0184 and 214.0128.

Figure 7:
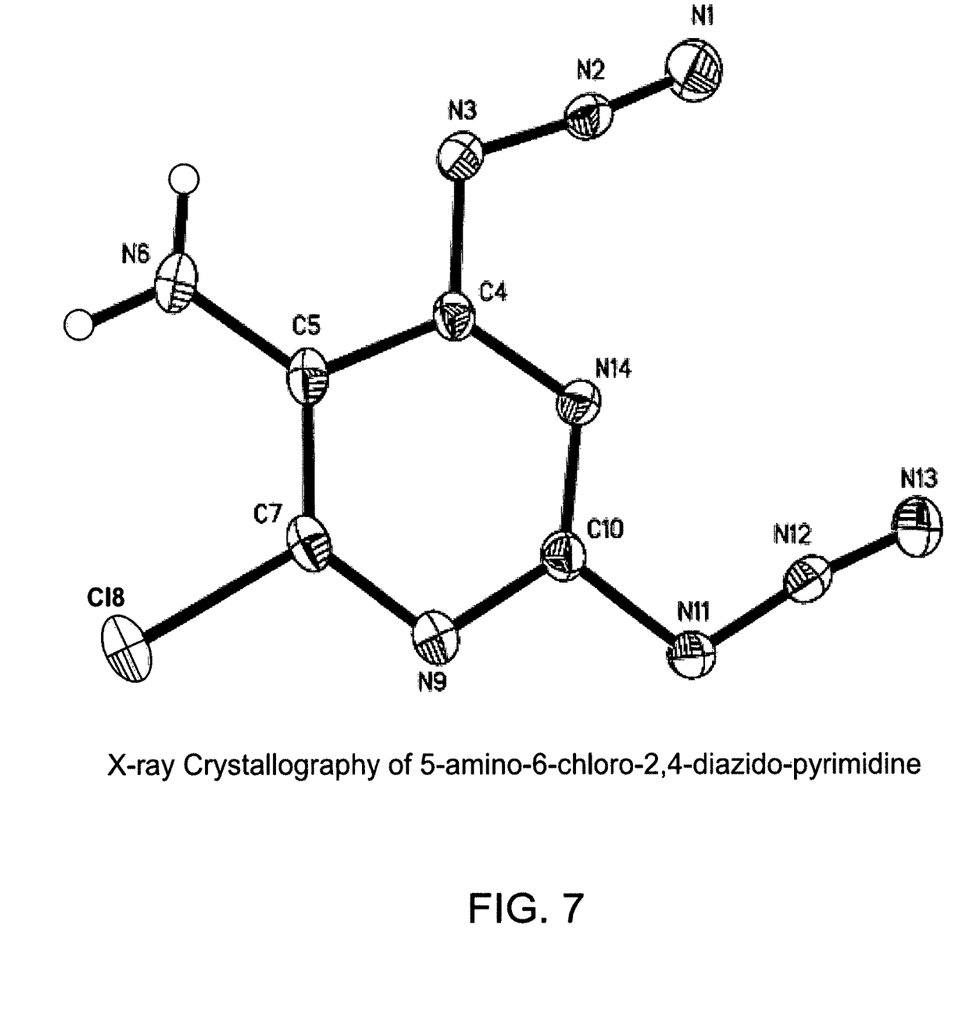
FIG. 7 is the X-ray crystallography of 5-amino-6-chloro-2,4-diazido-pyrimidine, alternatively as 5-amino-6-chloro-2,4-diazido-pyrimidin-5-amino, and as 5-amino-4-chloro-2,6-diazido-pyrimidine, alternatively as or 4-chloro-2,6-diazido-pyrimidin-5-amino.

X-ray crystallography performed by Dr. Greg H. Imler of the Naval Research Laboratory, 4555 Overlook Ave SW, Wash., D.C. 20375 confirmed the structure (See FIG. 7).

A source for one of the stating materials, 2,4,6-Trichloropyrimidin-5-amine, is available from eNovation Chemicals LLC, 173 Rock Rd, W. Green Brook, N.J. 08812 USA, under Product ID D508885, CAS #91322-00-8.

Actual Process. A process for synthesizing a chloro-azido-pyrimidin-5-amine includes:

forming in a volume of acetone a suspension comprising 5-amino-2,4,6-trichloropyrimidine and sodium azide, wherein there was an excess molar amount of sodium azide for each chloro group on the 5-amino-2,4,6-trichloropyrimidine.

Refluxing the suspension for about 12 to about 24 hours, wherein about 18 hours is optimum.

Filtering the suspension and collecting an oily filtrate, which was then concentrated forming a yellow-green oil. The sodium azide and a reaction by-product, sodium chloride, are both insoluble in acetone and were removed by the filtering. The fact that both the sodium azide and the formed sodium chloride are insoluble in acetone enables the 5-amino-6-chloro-2,4-diazido-pyrimidine to be readily isolated from potentially reactive agents. The dispersion is a two phase reaction, wherein 5-amino-2,4,6-trichloropyrimidine is dissolved in the acetone, which is the liquid phase and the sodium azide is insoluble in acetone and the excess sodium azide and the formed sodium chloride are solids in a non-miscible phase. Separation was easy and substantially complete. The acetone solution was concentrated to a yellow-green oil.

Dissolving the yellow-green oil in methylene chloride formed an organic solution.

Extracting the organic solution with water at least once; drying the organic solution over a drying agent, wherein the drying agent was sodium sulfate or a functionally equivalent drying agent.

Filtering the organic solution to remove the drying agent and any water, therein forming a dried filtrate, removing the methylene chloride by rotary evaporation to obtain an oil that is greater than 90% of 5-amino-6-chloro-2,4-diazido-pyrimidine with a theoretical crude yield of 100%.

Cooling the dried filtered oil to room temperature, which, after a few minutes at room temperature, turns into a yellow solid.

Dispersing the yellow solid in absolute ethanol forming a dispersion, and then gently heating the dispersion causing all of the yellow solid to dissolve forming a warm solution.

Cooling, covering and resting the warm solution overnight at ambient indoor conditions, therein providing conditions suitable for crystallization.

Collecting a filtride by filtration of the light yellow crystals that are formed.

Washing the light yellow crystals with very cold absolute ethanol, and drying the light yellow crystals of the chloro-azido-pyrimidin-5-amine, which is predominately 6-chloro-2,4-diazidopyrimidin-5-amine.

The synthesis produced 6-chloro-2,4-diazidopyrimidin-5-amine at a yield that is greater than 50%.

The excess molar amount of sodium azide for each chloro group on the 5-amino-2,4,6-trichloropyrimidine is about 2.5 equivalents of sodium azide for each equivalent of a chloro fraction of the 5-amino-2,4,6-trichloropyrimidine; or alternatively stated the molar ratio is about 7.6 moles of sodium azide per mole of 5-amino-2,4,6-trichloropyrimidine.

As previously noted, the synthesis step of filtering the suspension, removes the excess sodium azide and the formed sodium chloride from the suspension.

As previously disclosed in one exemplary embodiment, the amount of acetone is about 30 ml, sodium azide is about 2.5 g (about 38.0 mmol), and 5-amino-2,4,6-trichloropyrimidine is about 1.0 g (about 5.0 mmol).

The 6-chloro-2,4-diazidopyrimidin-5-amine may be oxidized to 6-chloro-2,4-dinitropyrimidine-5-amine, or reacted with another chloro compound using a coupling reaction. The amine may be reacted with an epoxy, an acid chloride like acryloyl chloride forming a monomer suitable for polymerization, or connected to a polyvinyl alcohol using a diisocyanate or reacted with at least one triazole.

It is to be understood that the foregoing description and specific exemplary embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

What is claimed is:

1. An azido amino-pyrimidine compound, consisting:

5-amino-6-chloro-2,4-diazido-pyrimidine.

2. The azido amino-pyrimidine compound according to claim 1, wherein said 5-amino-6-chloro-2,4-diazido-pyrimidine is crystalline and has a melting point of about 94-95° C.

3. A process for synthesizing a chloro-azido-pyrimidin-5-amine, comprising:
   forming in a volume of acetone a suspension comprising 5-amino-2,4,6-trichloropyrimidine and sodium azide, wherein an excess molar amount of sodium azide exists for each chloro fractional molar amount on the 5-amino-2,4,6-trichloropyrimidine;
   refluxing the suspension for about 12 to about 24 hours;
   filtering the suspension whereby the excess sodium azide and a reaction by-product, which is sodium chloride, are both insoluble in acetone and removed by said filtering, collecting the filtrate and concentrating it to a yellow-green oil;
   dissolving the yellow-green oil in methylene chloride forming an organic solution;
   extracting the organic solution with water at least once;
   drying the organic solution over a drying agent, wherein the drying agent is one of sodium sulfate and a functionally equivalent drying agent;
   filtering the organic solution for removing the drying agent and any water, therein forming a dried filtrate concentrated to an oil that has a weight greater than 90% of 5-amino-6-chloro-2,4-diazido-pyrimidine with a theoretical crude yield of 100%;
   cooling the oil to room temperature, which after a few minutes at room temperature turns into a yellow solid;
   dispersing the yellow solid in absolute ethanol forming a dispersion, and gently heating the dispersion causing all of the yellow solid to dissolve forming a warm solution;
   cooling, covering and resting the warm solution overnight at ambient indoor conditions, therein providing conditions suitable for crystallization;
   collecting by filtration light yellow crystals; and
   washing the light yellow crystals with very cold absolute ethanol, and drying the light yellow crystals of the chloro-azido-pyrimidin-5-amine, which is predominately 6-chloro-2,4-diazidopyrimidin-5-amine.

4. The process according to claim 3, wherein the synthesis produces 6-chloro-2,4-diazidopyrimidin-5-amine at a yield that is greater than 50%.

5. The process according to claim 3, wherein the excess molar amount of sodium azide for each chloro group on the 5-amino-2,4,6-trichloropyrimidine is a ratio of about 2.5 equivalents of sodium azide for each equivalent of a chloro fraction of the 5-amino-2,4,6-trichloropyrimidine, and wherein alternatively stated the molar ratio is about 7.6 moles of sodium azide per mole of 5-amino-2,4,6-trichloropyrimidine.

6. The process according to claim 3, wherein the step of filtering the suspension removes the sodium azide and the sodium chloride from the suspension.

7. The process according to claim 3, wherein the amount of acetone is about 30 ml, sodium azide is about 2.5 g (about 38.0 mmol), and 5-amino-2,4,6-trichloropyrimidine is about 1.0 g (about 5.0 mmol).

8. A process for synthesizing 5-amino-6-chloro-2,4-diazidopyrimidine, comprising:
   forming in a volume of acetone a suspension of 5-amino-2,4,6-trichloropyrimidine and sodium azide, wherein an excess molar amount of sodium azide exists for each chloro fractional molar amount of the 5-amino-2,4,6-trichloropyrimidine;
   refluxing the suspension for about 15 to about 20 hours;
   filtering the suspension and collecting a mixture of formed sodium chloride and excess sodium azide filtride and a filtrate, which is concentrated forming a yellow-green oil;
   dissolving the yellow-green oil in methylene chloride forming an organic solution;
   extracting the organic solution with water at least once;
   drying the organic solution over a drying agent, wherein the drying agent is one of sodium sulfate and a functionally equivalent drying agent;
   filtering the organic solution for removing, the drying agent and any water, therein forming a dried filtrate concentrated to an oil that has a weight greater than 90% of 5-amino-6-chloro-2,4-diazido-pyrimidine with a theoretical crude yield of 100%;
   cooling the oil to room temperature, which after a few minutes at room temperature turns into a yellow solid;
   dispersing the yellow solid in absolute ethanol forming a dispersion and gently heating the dispersion causing all of the yellow solid to dissolve forming a warm solution;
   cooling, covering and resting the warm solution overnight at ambient indoor conditions, therein providing conditions suitable for crystallization;
   collecting as a filtride by filtration the light yellow crystals that are formed; and
   washing the light yellow crystals with very cold absolute ethanol, and drying the light yellow crystals, which are about pure 5-amino-6-chloro-2,4-diazidopyrimidine, as the crystals have a melting point of about 94-95° C.

\* \* \* \* \*